United States Patent
Nakaya et al.

(10) Patent No.: US 12,098,150 B2
(45) Date of Patent: Sep. 24, 2024

(54) CRYSTAL OF HETEROCYCLIC AMIDE COMPOUND AND METHOD FOR PRODUCING SAME

(71) Applicant: NISSAN CHEMICAL CORPORATION, Tokyo (JP)

(72) Inventors: Yoshihiko Nakaya, Funabashi (JP); Youko Iyobe, Funabashi (JP); Takazumi Komuro, Funabashi (JP)

(73) Assignee: NISSAN CHEMICAL CORPORATION, Tokyo (JP)

( * ) Notice: Subject to any disclaimer, the term of this patent is extended or adjusted under 35 U.S.C. 154(b) by 610 days.

(21) Appl. No.: 17/439,526

(22) PCT Filed: Mar. 13, 2020

(86) PCT No.: PCT/JP2020/011226
§ 371 (c)(1),
(2) Date: Sep. 15, 2021

(87) PCT Pub. No.: WO2020/189576
PCT Pub. Date: Sep. 24, 2020

(65) Prior Publication Data
US 2022/0153736 A1    May 19, 2022

(30) Foreign Application Priority Data

Mar. 15, 2019  (JP) ................ 2019-048522

(51) Int. Cl.
*C07D 471/04* (2006.01)
*A01N 43/90* (2006.01)

(52) U.S. Cl.
CPC ........... *C07D 471/04* (2013.01); *A01N 43/90* (2013.01); *C07B 2200/13* (2013.01)

(58) Field of Classification Search
CPC .... C07D 417/04; A01N 43/90; C07B 2200/13
See application file for complete search history.

(56) References Cited

U.S. PATENT DOCUMENTS

2016/0108037 A1    4/2016  Nakaya et al.

FOREIGN PATENT DOCUMENTS

| JP | 2016-153397 A | 8/2016 |
|---|---|---|
| JP | 2017-025054 A | 2/2017 |
| JP | 2019-019118 A | 2/2019 |
| WO | 2014/192936 | * 12/2014 |
| WO | 2014/192936 A1 | 12/2014 |

OTHER PUBLICATIONS

Britta Olenik et al., "Polymorphism and the Organic Solid State: Influence on the Optimization of Agrochemicals", Modern Methods in Crop Protection Research, First Edition, 10 Theoretical Principles of Polymorphism, (2012), pp. 249-272.
Jan. 22, 2024 Office Action issued in Colombian Patent Application No. NC2021/0013450.
Apr. 24, 2024 Office Action issued in Japanese Patent Application No. 2021-507317.
Jun. 2, 2020 International Search Report issued in International Patent Application No. PCT/JP2020/011226.
Jun. 2, 2020 Written Opinion issued in International Patent Application No. PCT/JP2020/011226.

* cited by examiner

*Primary Examiner* — D Margaret M Seaman
(74) *Attorney, Agent, or Firm* — Oliff PLC (57) ABSTRACT

There is provided the crystal of a heterocyclic amide compound and a method for producing the same wherein the heterocyclic amide compound defined as a compound having useful activity as herbicide contains a novel crystal, as shown in formula (1):

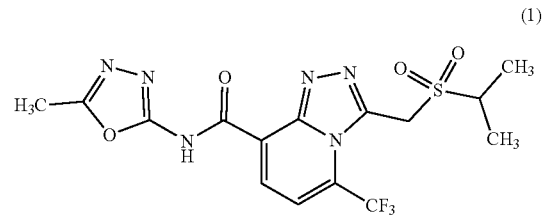

3 Claims, 2 Drawing Sheets

CRYSTAL OF HETEROCYCLIC AMIDE COMPOUND AND METHOD FOR PRODUCING SAME

TECHNICAL FIELD

The present invention relates to a novel crystal of 3-[(isopropylsulfonyl)methyl]-N-(5-methyl-1,3,4-oxadiazole-2-yl)-5-(trifluoromethyl)-[1,2,4]triazolo[4,3-a]pyridine-8-carboxamide [hereinafter abbreviated as Compound (1)] and a method for producing the crystal.

(1)

BACKGROUND ART

A solid state of a chemical compound can be amorphous (that is, there is no long-range order in the distance of atoms) or crystalline (that is, atoms are arranged in an ordered reflection pattern). In addition, it is still impossible to predict physico-chemical properties such as a melting point or solubility related to a crystal form in which a chemical compound can be in a solid state. In addition, it is still difficult to predict whether a solid state of a compound is amorphous or crystalline.

On the other hand, Compound (1) of the present invention is known as a heterocyclic amide compound that is useful as an herbicide (for example, refer to Patent Document 1 to Patent Document 4).

PRIOR ART DOCUMENTS

Patent Document 1: WO 2014/192936
Patent Document 2: JP2016-153397A
Patent Document 3: JP 2017-025054A
Patent Document 4: JP2019-019118A

SUMMARY OF THE INVENTION

In general, it is still impossible to produce a specific crystal of a compound and to predict physical properties such as a melting point and water solubility of the obtained crystal.

The present invention provides a novel crystal of Compound (1) and a method for producing the same.

The inventors conducted extensive studies, and as a result, found that Compound (1) has a novel crystal. That is, the present invention relates to a crystal of Compound (1) described in the following [1] to [4] (hereinafter abbreviated as a crystal of the present invention), a composition including the crystal of the present invention described in the following [5] to [8] (hereinafter abbreviated as a composition of the present invention), and a weed control method using the crystal of the present invention described in the following [9] and [10].

[1] A crystal of a heterocyclic amide compound represented by Formula (1), which has peaks at a diffraction angle 2θ of 7.29°±0.2, 12.62°±0.2, 14.13°±0.2, 17.51°±0.2, 18.64°±0.2, 19.03°±0.2, 20.56°±0.2, 20.89°±0.2, 21.76°±0.2, 23.37°±0.2, 25.41°±0.2, 27.70°±0.2 and 30.34°±0.2 in powder X-ray diffraction with Cu-Kα rays:

(1)

[2] A crystal of a heterocyclic amide compound represented by Formula (1), which has peaks at a diffraction angle 2θ of 7.29°±0.1, 12.62°±0.1, 14.13°±0.1, 17.51°±0.1, 18.64°±0.1, 19.03°±0.1, 20.56°±0.1, 20.89°±0.1, 21.76°±0.1, 23.37°±0.1, 25.41°±0.1, 27.70°±0.1, and 30.34°±0.1 in powder X-ray diffraction with Cu-Kα rays:

(1)

[3] A crystal of a heterocyclic amide compound represented by Formula (1), which has peaks at a diffraction angle 2θ of 7.29°, 12.62°, 14.13°, 17.51°, 18.64°, 19.03°, 20.56°, 20.89°, 21.76°, 23.37°, 25.41°, 27.70°, and 30.34° in powder X-ray diffraction with Cu-Kα rays:

(1)

Figure 1:
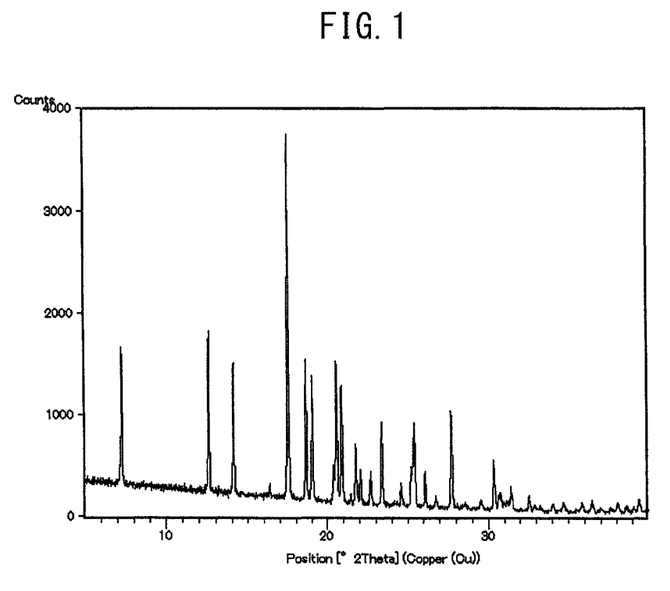
FIG. 1 is a powder X-ray diffraction chart of a crystal of the present invention.

[4] The crystal of the heterocyclic amide compound according to any one of [1] to [3], wherein, in the powder X-ray diffraction with Cu-Kα rays, substantially the same diffraction curve as in FIG. 1 of the present application is shown.
[5] An agrochemical composition including the crystal according to any one of [1] to [3].
[6] An herbicide composition including the crystal according to any one of [1] to [3].
[7] A suspension composition including the crystal according to any one of [1] to [3], and a dispersion medium.
[8] An aqueous suspension composition including the crystal according to any one of [1] to [3], a surfactant and water as a dispersion medium.

[9] A weed control method including a process of applying the composition according to any one of [5] to [8] in an amount effective for controlling weeds.

[10] The weed control method according to [9], including a process of spraying the composition according to any one of [5] to [8] in an amount effective for controlling weeds on stems and leaves.

According to the present invention, it is possible to obtain a crystal of Compound (1) with good reproducibility.

MODES FOR CARRYING OUT THE INVENTION

Compound (1) is 3-[(isopropylsulfonyl)methyl]-N-(5-methyl-1,3,4-oxadiazole-2-yl)-5-(trifluoromethyl)-[1, 2,4]triazolo[4,3-a]pyridine-8-carboxamide, and the structure thereof is shown below.

(1)

Powder X-ray diffraction peaks of a crystal of the present invention are shown below. $2\theta$=7.29°, 12.62°, 14.13°, 17.51°, 18.64°, 19.03°, 20.56°, 20.89°, 21.76°, 23.37°, 25.41°, 27.70°, 30.34°.

In addition, since the error of the powder X-ray diffraction peak can usually be ±0.2, and in some cases ±0.1, the peak values of the crystal of the present invention in consideration of the error are usually $2\theta$=7.29°±0.2, 12.62°±0.2, 14.13°±0.2, 17.51°±0.2, 18.64°±0.2, 19.03°±0.2, 20.56°±0.2, 20.89°±0.2, 21.76°±0.2, 23.37°±0.2, 25.41°±0.2, 27.70°±0.2, and 30.34°±0.2, and in some cases $2\theta$=7.29°±0.1, 12.62°±0.1, 14.13°±0.1, 17.51°±0.1, 18.64°±0.1, 19.03°±0.1, 20.56°±0.1, 20.89°±0.1, 21.76°±0.1, 23.37°±0.1, 25.41°±0.1, 27.70°±0.1, and 30.34°±0.1.

Measurement conditions for the powder X-ray diffraction peaks shown above are as follows.
[Powder X-Ray Diffraction]
   Device: X'PERT-PRO MPD (commercially available from Spectris)
   Measurement method: transmission method
   X rays: Cu-Kα
   Voltage: 45 kV
   Current: 40 mA
   Sampling interval: 0.0070 deg
   Data range: $2\theta$=5 deg to 40 deg The crystal of the present invention has a melting point of 216° C. to 218° C., and no endothermic peak is observed in a lower temperature range than the melting point in the differential scanning calorimetry.

The conditions for differential scanning calorimetry in the melting point measurement shown above are as follows.
[Differential Scanning Calorimetry Condition]
   Device: DSC-60 (commercially available from Shimadzu Corporation)
   Temperature rise: 20° C.-(10° C./min)-450° C.
   Atmosphere: nitrogen
   Control: $Al_2O_3$
   Container: made of SUS
   Sampling: 1 sec Next, a method for producing the crystal of the present invention will be described below.

A crystal of the present invention is obtained by a method in which Compound (1) is heated and dissolved in a solvent, and the obtained solution is gradually cooled and crystallized or a method in which the solvent is distilled off from the obtained solution and crystallized. The solvent used may be any solvent that is inactive to Compound (1). For example, ether solvents such as diethyl ether, methyl-t-butyl ether, tetrahydrofuran, dimethoxymethane, diethoxymethane, 1,2-dimethoxyethane, ethylene glycol dimethyl ether, ethylene glycol diethyl ether, ethylene glycol dibutyl ether, diethylene glycol dimethyl ether, diethylene glycol diethyl ether, diethylene glycol dibutyl ether, triethylene glycol dimethyl ether, and 1,4-dioxane, alcohol solvents such as methanol, ethanol, 1-propanol, 2-propanol, 1-butanol, 2-butanol, isobutanol, 2-methyl-2-propanol, methyl cellosolve, ethyl cellosolve, i-propyl cellosolve, diethylene glycol monomethyl ether, diethylene glycol monoethyl ether, diethylene glycol monobutyl ether, cyclohexanol, and benzyl alcohol, aliphatic hydrocarbon solvents such as n-pentane, n-hexane, cyclohexane, methylcyclohexane, n-heptane, n-octane, and n-decane, aromatic hydrocarbon solvents such as benzene, toluene, xylene, chlorobenzene, o-dichlorobenzene, m-dichlorobenzene, p-dichlorobenzene, nitrobenzene, and tetrahydronaphthalene, nitrile solvents such as acetonitrile and propionitrile, ester solvents such as methyl acetate, ethyl acetate, butyl acetate, and ethyl propionate, halogenated hydrocarbon solvents such as methylene chloride, chloroform, carbon tetrachloride, 1,2-dichloroethane, and 1,1,2-trichloroethane, amide solvents such as N,N-dimethylformamide, N,N-dimethylacetamide, and N-methylpyrrolidone, urea solvents such as 1,3-dimethylimidazolidinone, and N,N,N',N'-tetramethylurea, sulfur-containing polar solvents such as dimethyl sulfoxide and sulfolane, pyridine solvents such as pyridine, 2-picoline, 3-picoline, 4-picoline, and 5-ethyl-2-picoline, ketone solvents such as acetone, methyl ethyl ketone, diethyl ketone, and methyl isobutyl ketone, and water can be used, and these solvents may be used alone or two or more thereof may be used in combination. Among these solvents, ether solvents, aromatic hydrocarbon solvents, ester solvents, halogenated hydrocarbon solvents, and amide solvents are preferable, and 1,4-dioxane, toluene, ethyl acetate, 1,2-dichloroethane, and N,N-dimethylformamide are more preferable.

The amount of the solvent used is usually 0.5 parts by weight to 50 parts by weight and preferably 1 part by weight to 30 parts by weight with respect to 1 part by weight of Compound (1).

The temperature at which Compound (1) is dissolved in a solvent is usually 30° C. to 150° C., and preferably 30° C. to 100° C.

The cooling rate is usually 0.1° C./hour to 80° C./hour, and preferably 1° C./hour to 60° C./hour, and can be changed to any cooling rate within the above range at any time.

The temperature of the solution when the precipitated crystal is taken out is usually −30° C. to 50° C., and preferably −20° C. to 30° C.

The time required for crystallization is usually 0.1 hours to 100 hours, and preferably 1 hour to 50 hours.

In addition, when the solvent is distilled off, it can be distilled off by heating it to a boiling point of the solvent or higher under atmospheric pressure. In addition, when the decompression degree in the container is adjusted, the solvent can be distilled off at any temperature up to the boiling point of the solvent under a reduced pressure.

Compared with the amorphous Compound (1), for example, the crystal of the present invention has excellent properties such as chemical stability, light stability, hygroscopicity, suspensibility, and filterability, and has excellent production properties such as removability of the residual solvent.

Next, a composition of the present invention will be described in detail.

When the composition of the present invention is an aqueous suspension agrochemical composition, water or an organic liquid in which the crystal of the present invention is unlikely to dissolve can be used as a dispersion medium that can be used. Examples of organic liquids include alcohols such as ethylene glycol, diethylene glycol, propylene glycol, dipropylene glycol and isopropanol, ethers such as butyl cellosolve, ketones such as cyclohexanone, esters such as γ-butyrolactone, acid amides such as N-methylpyrrolidone and N-octylpyrrolidone, aromatic hydrocarbons such as xylene, alkylbenzenes, phenylxylylethane and alkylnaphthalenes, aliphatic hydrocarbons such as machine oil, normal paraffin, isoparaffin and naphthene, mixtures of aromatic hydrocarbons such as kerosene and aliphatic hydrocarbons, and oils and fats such as soybean oil, linseed oil, rapeseed oil, coconut oil, cottonseed oil and castor oil.

The content of the crystal of the present invention with respect to 100 parts by weight of the composition of the present invention is usually 0.1 parts by weight to 50 parts by weight, and more preferably 1 part by weight to 30 parts by weight.

In addition, in addition to the crystal of the present invention, it is possible to additionally include one or more known agrochemicals, for example, an herbicide, a safener, a pesticide, an acaricide, a nematicide, an antiviral agent, a plant growth regulator, a bactericide, a synergist, an attractant and a repellent, and in this case, a better preventive effect can be exhibited. Particularly preferable known agrochemicals include an herbicide, a safener, a bactericide, a nematicide and a pesticide. Specific examples of common names are as follows, but the names are not necessarily limited thereto.

Herbicides: 4-CPA, 4-CPA-salts, 4-CPB, 4-CPP, 2,4-D (2,4-PA), 2,4-D-salts, 2,4-D-esters, 3,4-DA, 2,4-DB, 2,4-DB-salts, 2,4-DB-esters, 3,4-DB, 2,4-DEB, 2,4-DEP, 3,4-DP, 2,4,5-T, 2,4,5-T-salts, 2,4,5-T-esters, 2,4,5-TB, 2,3,6-TBA (TCBA), 2,3,6-TBA-salts, acetochlor, acifluorfen, acifluorfen-methyl, acifluorfen-sodium, aclonifen, acrolein, alachlor, allidochlor (CDAA), alloxydim, alloxydim-sodium, allyl alcohol, alorac, ametridione, ametryn, amibuzin, amicarbazone, amidochlor, amidosulfuron, aminocyclopyrachlor, aminocyclopyrachlor-methyl, aminocyclopyrachlor-potassium, aminopyralid, aminopyralid-salts, amiprophos, amiprophos-methyl, amitrole (aminotriazole, ATA), ammonium sulfamate (AMS), anilofos, anisuron, asulam, asulam-salts, atraton, atrazine, azafenidin, azimsulfuron, aziprotryne (azyprotryn), barban (CBN), 1BCPC, beflubutamid, beflubutamid-M, benazolin, benazolin-ethyl, benazolin-salts, bencarbazone, benfluralin (benefin), benfuresate, bensulfuron, bensulfuron-methyl, bensulide (SAP), bentazon (bentazone), bentazone-sodium, bentranil, benzadox, benzadox-ammonium, benzfendizone, benzipram, benzobicyclon, benzofenap, benzofluor, benzoylprop, benzoylpropethyl, benzthiazuron, bicyclopyrone, bifenox, bilanafos (bialaphos), bilanafos-sodium, binapacryl, bispyribac, bispyribac-sodium, bixlozone, borax, bromacil, bromacil-salts, bromobonil, bromobutide, bromofenoxim, bromopyrazon, bromoxynil, bromoxynil-potassium, bromoxynil-esters, butachlor, butafenacil, butamifos, butenachlor, butralin (butraline), buthidazole, buthiuron, butroxydim, buturon, butylate, cafenstrole, calcium cyanamide, cambendichlor, calcium chlorate, carbasulam, carbetamide, carboxazole, carfentrazone, carfentrazone-ethyl, CDEA, CEPC, chlomethoxyfen (chlomethoxynil), chloramben, chloramben-salts, chloramben-methyl, chloramben-methylammonium, chloranocryl (dicryl), chlorazifop, chlorazifop-propargyl, chlorazine, chlorbromuron, chlorbufam (BIPC), chloreturon, chlorfenac (fenac), chlorfenac-salts, chlorfenprop, chlorfenprop-methyl, chlorflurazole, chlorflurenol, chlorflurenol-methyl, chloridazon (PAC, pyrazon), chlorimuron, chlorimuron-ethyl, chlornidine, chlornitrofen (CNP), chloroacetic acid (monochloroacetic acid), sodium chloroacetate (SMA), chlorotoluron, chloroxuron, chloroxynil, chlorprocarb, chlorphtalim, chlorpropham (IPC), chlorsulfuron, chlorthal (TCTP), chlorthal-esters, chlorthiamid (DCBN), cinidon-ethyl, cinmethylin, cinosulfuron, cisanilide, clacyfos, clethodim, cliodinate, clodinafop, clodinafop-propargyl, clofop, clofop-isobutyl, clomazone, clomeprop, cloprop, cloproxydim, clopyralid, clopyralid-methyl, clopyralid-salts, cloransulam, cloransulam-methyl, (divalent) copper sulfate, CPMF, CPPC, credazine, cresol, cumyluron, cyanatryn, cyanamide, cyanazine, cycloate, cyclopyranil, cyclopyrimorate, cyclosulfamuron, cycloxydim, cycluron (COMU), cyhalofop, cyhalofop-butyl, cyperquat, cyperquat-chloride, cyprazine, cyprazole, cypromid, daimuron (dymron), dalapon, dalapon-salts, dazomet, dazomet-sodium, delachlor, desmedipham, desmetryn, di-allate, dicamba (MDBA), dicamba-salts, dicamba-esters, dichlobenil (DBN), dichloraurea (DCU), dichlormate, o-dichlorobenzene (DCB), dichlorprop, dichlorprop-salts, dichlorprop-esters, dichlorprop-P, dichlorprop-P-salts, dichlorprop-P-esters, diclofop, diclofop-methyl, diclofop-P, diclofop-P-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-p, dimexano, dimidazon, dimethyl disulfide, dinitramine, dinofenate, dinoprop, dinosam, dinoseb (DNBP), dinoseb-salts, dinoseb-esters, dinoterb, dinoterb-salts, dinoterb-esters, diphenamid, dipropalin, dipropetryn, diquqt, diquqt dibromide, disul(2,4-PS), disul-sodium, dithiopyr, diuron (DCMU), DMPA, DNOC, DNOC-salts, EBEP, eglinazine, eglinazine-ethyl, endothal, endothal-salts, epronaz, EPTC, erbon, esprocarb, ethachlor, ethalfluralin, ethametsulfuron, ethametsulfuron-methyl, ethaprochlor, ethidimuron, ethiolate, ethiozin, ethofumesate, ethoxyfen, ethoxyfen-ethyl, ethoxysulfuron, etinofen, etnipromid, etobenzanid, EXD, fenasulam, fenoprop (2,4,5-TP, silvex), fenoprop-salts, fenoprop-esters, fenoxaprop, fenoxaprop-ethyl, fenoxaprop-p, fenoxaprop-p-ethyl, fenoxasulfone, fenquinotrione, fenteracol, fenthiaprop, fenthiaprop-ethyl, fentrazamide, (divalent) ferrous sulfate, fenuron, fenuron-TCA, flamprop, flamprop-esters, flamprop-M, flamprop-M-esters, flazasulfuron, florasulam, florpyrauxifen, florpyrauxifen-benzyl, fluazifop, fluazifop-esters, fluazifop-P, fluazifop-p-esters, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen (CFNP), fluothiuron, flupoxam, flupropacil, flupropanate (tetrapion), flupropanate-sodium, flupyrsulfuron, flupyrsulfuron-methyl, flupyrsulfuron-sodium, flupyrsulfuron-methyl-sodium, fluridone, flurochloridone, fluroxypyr, fluroxypyr-esters, flurtamone, fluthiacet, fluthiacet-methyl, fomesafen, fomesafen-sodium, foramsulfuron, fosamine, fosamine-ammonium, furyloxyfen, glufosinate, glufosinate-salts, glufosinate-P, glufosinate-P-salts, glyphosate, glyphosate-salts, halauxifen, halauxifen-methyl, halosafen, halosulfuron, halosulfuron-methyl, haloxydine, haloxyfop, haloxyfop-sodium, haloxyfop-esters, haloxyfop-P, haloxyfop-p-esters, herbimycin, hexachloroacetone (HCA), hexazinone, imazamethabenz, imazamethabenz-methyl, imazamox, imazamox-ammonium, imazapic, imazapic-ammonium, imazapyr, imazapyr-isopropylammonium, imazaquin, imazaquin-methyl, imazaquin-salts, imazethapyr, imazethapyr-ammonium, imazosulfuron, indanofan, indaziflam, iodobonil, iodosulfuron, iodosulfuron-sodium, iodosulfuron-methyl, iodosulfuron-methyl-sodium, iofensulfuron, iofensulfuron-sodium, ioxynil, ioxynil-salts, ioxynil-esters, ipazine, ipfencarbazone, iprymidam, isocarbamid, isocil (isoprocil), isomethiozin, isonoruron, isopolinate, isopropalin, isoproturon, isouron, isoxaben, isoxachlortole, isoxaflutole, isoxapyrifop, karbutilate, ketospiradox, ketospiradox-potassium, lactofen, lancotrione, lancotrione-sodium, lenacil, linuron, MCPA, MCPA-salts, MCPA-esters, MCPB, MCPB-salts, MCPB-esters, mecoprop (MCPP), mecoprop-salts, mecoprop-esters, mecoprop-P, mecoprop-P-salts, mecoprop-P-esters, medinoterb, medinoterb acetate, mefenacet, mefluidide, mefluidide-salts, mesoprazine, mesosulfuron, mesosulfuron-methyl, mesotrione, metam (carbam), metam-salts, metamifop, metamitron, metazachlor, metazosulfuron, metflurazon, methabenzthiazuron (methibenzuron), methalpropalin, methazole, methiobencarb, methiuron, methometon, methoprotryne (methoprotryn), methoxyphenone, methiopyrisulfuron, methiozolin, methyl azide, methyl bromide, methyl dymron, methyl iodide, methyl isothiocyanate, metobenzuron, metobromuron, metolachlor, S-metolachlor, metosulam, metoxuron, metribuzin, metsulfuron, metsulfuron-methyl, molinate, monalide, monisouron, monolinuron, monosulfuron, monosulfuron-methyl, monuron (CMU), monuron-TCA, morfamquat, morfamquat dichloride, naproanilide, napropamide, napropamide-M, naptalam (NPA), naptalam-sodium, neburon, nicosulfuron, nipyraclofen, nitralin, nitrofen (NIP, niclofen), nitrofluorfen, norflurazon, noruron (norea), OCH, oleic acid, orbencarb, orthosulfamuron, oryzalin, oxadiargyl, oxadiazon, oxapyrazon, oxapyrazon-salts, oxasulfuron, oxaziclomefone, oxyfluorfen, parafluron, paraquat, paraquat dichloride, paraquat dimetilsulfate, pebulate, pelargonic acid (nonanoic acid), pendimethalin, penoxsulam, pentachlorophenol, sodium pentachlorophenoxide, pentachlorophenyl laurate, pentanochlor (solan, CMMP), pentoxazone, perfluidone, pethoxamid, phenisopham, phenmedipham, phenmedipham-ethyl, phenobenzuron, picloram, picloram-salts, picloram-esters, picolinafen, pinoxaden, piperophos, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn (prometryne), propachlor, propanil (DCPA), propaquizafop, propazine, propham, propisochlor, propoxycarbazone, propoxycarbazone-sodium, propyrisulfuron, propyzamide (pronamide), prosulfalin, prosulfocarb, prosulfuron, proxan (IPX), proxan-sodium, prynachlor, pydanon, pyraclonil, pyraflufen, pyraflufen-ethyl, pyrasulfotole, pyrazolynate (pyrazolate), pyrazosulfuron, pyrazosulfuron-ethyl, pyrazoxyfen, pyribambenz-isopropyl, pyribambenz-propyl, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinclorac-dimethylammonium, quinclorac-methyl, quinmerac, quinoclamine (ACN), quinonamid, quizalofop, quizalofop-esters, quizalofop-P, quizalofop-P-esters, rhodethanil, rimsulfuron, saflufenacil, sebuthylazine, secbumeton, sethoxydim, siduron, simazine (CAT), simeton, simetryn (simetryne), sodium azide, sodium chlorate, sulcotrione, sulfallate (CDEC), sulfentrazone, sulfometuron, sulfometuron-methyl, sulfosulfuron, sulfuric acid, sulglycapin, swep (MCC), tavron, TCA (trichloroacetic acid), TCA-salts, TCA-ethadyl, tebutam (butam), tebuthiuron, tefuryltrione, tembotrione, tepraloxydim, terbacil, terbucarb (terbutol, MPMC), terbuchlor, terbumeton, terbuthylazine, terbutryn, tetflupyrolimet, tetrafluron, thenylchlor, thiazafluron, thiazopyr, thidiazimin, thidiazuron, thiencarbazone, thiencarbazone-methyl, thifensulfuron, thifensulfuron-methyl, thiobencarb (benthiocarb), tiafenacil, tiocarbazil, tioclorim, tolpyralate, topramezone, tralkoxydim, triafamone, triallate (tri-allate), triasulfuron, triaziflam, tribenuron, tribenuron-methyl, tricamba, triclopyr, triclopyr-salts, triclopyr-esters, tridiphane, trietazine, trifloxysulfuron, trifloxysulfuron-sodium, trifludimoxadin, trifluralin, triflusulfuron, triflusulfuron-methyl, trifop, trifop-methyl, trifopsime, trihydroxytriazine (cyanuric acid), trimeturon, tripropindan, tritac, tritosulfuron, vernolate, xylachlor, dimesulfazet, 6-{(difluoromethyl)thio}-N2,N4-diisopropyl-1,3,5-triazine-2,4-diamine (CAS 103427-73-2), (R)-2-[{7-(2-chloro-4-(trifluoromethyl)phenoxy)naphthalene-2-yl} oxy]methyl propanoate (CAS 103055-25-0), propane-2-one O-(12H-dibenzo [d, g] [1,3]dioxocin-6-carbonyl)oxime (CAS 503819-68-9), [{(2-(N-methylmethylsulfonamide)-2-oxoethyl)amino}methyl]phosphonate (CAS 98565-18-5), 2-[{2-(4-((6-chloroquinoxaline-2-yl)oxy)phenoxy) propanoyl}oxy]-3-methyl-3-ethyl butanoate (CAS 1191932-79-2), 2-(3,7-dichloroquinoline-8-carbonyl)-3-hydroxy-2-cyclohexen-1-one (CAS 1350901-36-8), O-(2,4-dimethyl-6-nitrophenyl) O-methylisopropylphosphoramide thioate (CAS 189517-75-7), 5-[N-(4,6-dimethylpyrimidine-2-yl)carbamoyl}sulfamoyl]-1-(pyridine-2-yl)-1H-methyl pyrazole-4-carboxylate (CAS 104770-29-8), 4-[2-chloro-3-(3,5-dimethyl-1H-pyrazol-1-yl)methyl]-4-(methyl sulfonyl) benzoyl]-1,3-di methyl-1H-pyrazole-5-yl 1,3-dimethyl-1H-pyrazole-4-carboxylate (CAS 1911613-97-2), 4-[2-chloro-4-(methyl sulfonyl)-3-{(2,2,2-trifluoroethoxy) methyl}benzoyl]-1-ethyl-1H-pyrazole-5-yl 1,3-dimethyl-1H-pyrazole-4-carboxylate (CAS 1992017-55-6), 1-{2-chloro-3-(3-cyclopropyl-5-hydroxy-1-methyl-1H-pyrazole-4-carbonyl)-6-(trifluoro methyl)phenyl}piperidine-2-one (CAS 1855929-45-1), 1,3-dimethyl-4-{2-(methyl sulfonyl)-4-(trifluoromethyl)benzoyl}-1H-pyrazole-5-yl 1,3-dimethyl-1H-pyrazole-4-carboxylate (CAS 1622908-18-2), 2-[{3-(2-chloro-4-fluoro-5-(3-methyl-2,6-dioxo-4-(trifluoromethyl)-3,6-dihydropyrimidine-1(2H)-yl))phenoxy)pyridine-2-yl}oxy]ethylacetate (CAS 353292-31-6), 2-methyl- N-(5-methyl-1,3,4-oxadiazole-2-yl)-3-(methylsulfonyl)-4-(trifluoromethyl)benz amide (CAS 1400904-50-8), 2-chloro-N-(1-methyl-1H-tetrazole-5-yl)-3-(methylthio)-4-(trifluoromethyl)benzamide (CAS 1361139-71-0), 2-chloro-N-(1-methyl-1H-tetrazole-5-yl)-3-(methyl sulfonyl)-4-(trifluoromethyl)benzamide (CAS 1361139-73-2), 4-(4-fluorophenyl)-6-(2-hydroxy-6-oxo-1-cyclohexene-1-carbonyl)-2-methyl-1,2,4-triazine-3,5 (2H,4H)-dione (CAS 1353870-34-4), F4050 (test name), F9960 (test name), OK-701 (test name), SL-1201(test name), and the like.

Safeners: benoxacor, BPCMS (CSB), cloquintocet, cloquintocet-mexyl, cumyluron, cyometrinil, cyprosulfamide, daimuron (dymron), dichlormid, dicyclonon (diclonon), dietholate, dimepiperate, disulphoton, fenchlorazole, fenchlorazole-ethyl, fenclorim, flurazole, fluxofenim, furilazole, hexim, isoxadifen, isoxadifen-ethyl, MCPA, mecoprop, mefenpyr, mefenpyr-diethyl, mephenate, metcamifen, methoxyphenone, 1,8-naphthalic anhydride (NA), octamethylene-diamine, oxabetrinil, 4-(dichloroacetyl)-1-oxa-4-azaspiro[4.5]decane (AD67, MON4660), 4-carboxy-3,4-dihydro-2H-1-benzopyran-4-acetic acid (CL304415), 2,2-dichloro-N-[2-oxo-2-(propenylamino)ethyl]-N-2-propenylacetamide (DKA-24), 2-(dichloromethyl)-2-methyl-1,3-dioxolane (MG191), 2-propenyl 1-oxa-4-azaspiro[4,5]decane-4-carbodithioate (MG838), (3-dichloroacetyl-5-(2-furyl)-2,2-dimethyloxazoxidine) (MON13900), (N-allyl-N-[(1,3-dioxolane-2-yl)methyl]dichloroacetamide (PPG-1292), 3-(dichloroacetyl)-2,2-dimethyl-1,3-oxazolidine (R28725), 3-(dichloroacetyl)-2,2,5-trimethyl-1,3-oxazolidine (R29148), 1-dichloroacetyl azepane (TI-35), and the like.

Bactericides: acibenzolar-S-methyl, acypetacs, aldimorph, allyl alcohol, ametoctradin, aminopyrifen, amisulbrom, amobam, ampropylfos, anilazine, azaconazole, azithiram, azoxystrobin, barium polysulfide, benalaxyl, benalaxyl-M, benodanil, benomyl, benquinox, bentaluron, benthiavalicarb-isopropyl, benthiazole, benzamacril, benzamorf, benzovindiflupyr, binapacryl, biphenyl, bitertanol, bixafen, blasticidin-S, bordeaux mixture, boscalid, bromoconazole, bupirimate, buthiobate, butylamine, lime sulfur (calcium polysulfide), captafol, captan, carbamorph, carbendazim, carboxin, carpropamid, carvone, cheshunt mixture, chinomethionat, chlobenthiazone, chloraniformethane, chloranil, chlorfenazole, chloroneb, chloropicrin, chlorothalonil, chlorquinox, chlozolinate, climbazole, copper acetate, copper carbonate (basic), copper hydroxide, copper naphthenate, copper oleate, copper oxychloride, copper sulfate, copper sulfate (basic), copper zinc chromate, coumoxystrobin, cresol, cufraneb, cuprobam, cyazofamid, cyclafuramid, cycloheximide, cyflufenamid, cymoxanil, cypendazole, cyproconazole, cyprodinil, cyprofuram, dazomet, debacarb, decafentin, dehydroacetic acid, dichlobentiazox, dichlofluanid, dichlone, dichlorophen, dichlozoline, diclobutrazol, diclocymet, diclomezine, dicloran, diethofencarb, difenoconazole, diflumetorim, dimethirimol, dimethomorph, dimoxystrobin, diniconazole, diniconazole-M, dinobuton, dinocap, dinocap-4, dinocap-6, dinocton, dinosulfon, dinoterbon, diphenylamine, dipymetitrone, dipyrithione, disulfiram, ditalimfos, dithianon, DNOC, dodemorph, dodine, drazoxolon, edifenphos, enestrobin, enoxastrobin, epoxiconazole, ethaboxam, etaconazole, etem, ethirimol, ethoxyquin, etridiazole, famoxadone, fenamidone, fenaminosulf, fenaminstrobin, fenapanil, fenarimol, fenbuconazole, fenfuram, fenhexamid, fenitropan, fenoxanil, fenpiclonil, fenpicoxamid, fenpropidin, fenpropimorph, fenpyrazamine, fentin, ferbam, ferimzone, florylpicoxamid, fluazinam, fludioxonil, flufenoxystrobin, fluindapyr, flumetover, flumorph, fluopicolide, fluopimomide, fluopyram, fluoroimide, fluotrimazole, fluoxapiprolin, fluoxastrobin, fluquinconazole, flusilazole, flusulfamide, flutolanil, flutianil, flutriafol, fluxapyroxad, folpet, fosetyl-aluminium, fthalide, fuberidazole, furalaxyl, furametpyr, furcarbanil, furconazole, furconazole-cis, furmecyclox, furophanate, glyodin, griseofulvin, guazatine, halacrinate, hexachlorobenzene, hexaconazole, hexylthiofos, oxyquinoline sulfate (8-hydroxyquinoline sulfate), hymexazol, imazalil, imibenconazole, iminoctadine-albesilate, iminoctadine-triacetate, inpyrfluxam, iodocarb, ipconazole, ipfentrifluconazole, ipflufenoquin, iprobenfos, iprodione, iprovalicarb, isofetamid, isoflucypram, isotianil, isoprothiolane, isopyrazam, isovaledione, kasugamycin, kresoxim-methyl, laminarin, mancopper, mancozeb, mandestrobin, mandipropamid, maneb, mebenil, mecarbinzid, mefentrifluconazole, mepanipyrim, mepronil, meptyldinocap, metalaxyl, metalaxyl-M, metam, metazoxolon, metconazole, methasulfocarb, methfuroxam, metyltetraprole, metiram, metominostrobin, metrafenone, metsulfovax, milneb, myclobutanil, myclozolin, nabam, naftifine, natamycin, organic nickel (nickel bis (dimethyldithiocarbamate)), nitrostyrene, nitrothal-isopropyl, nuarimol, octhilinone, ofurace, orysastrobin, oxadixyl, oxathiapiprolin, oxine copper, oxpoconazole fumarate, oxycarboxin, pefurazoate, penconazole, pencycuron, penflufen, pentachlorophenol, penthiopyrad, orthophenylphenol (2-phenylphenol), phosdiphen, phthalide, picarbutrazox, picoxystrobin, piperalin, polycarbamate, polyoxins, polyoxin-D (polyoxorim), potassium azide, potassium hydrogen carbonate, probenazole, prochloraz, procymidone, propamocarb hydrochloride, propiconazole, propineb, proquinazid, prothiocarb, pyrazophos, pyribencarb, pyrifenox, pyrimethanil, pyriminostrobin, pyroquilon, prothiocarb, prothioconazole, pydiflumetofen, pyracarbolid, pyraclostrobin, pyrametostrobin, pyraoxystrobin, pyrapropoyne, pyraziflumid, pyridachlometyl, pyridinitril, pyriofenone, pyrisoxazole, pyroxychlor, pyroxyfur, quinacetol-sulfate, quinazamid, quinconazole, quinoxyfen, quinofumelin, quintozene, rabenzazole, salicylanilide, sedaxane, silthiofam, simeconazole, sodium hydrogen carbonate, sodium hypochlorite, spiroxamine, sulfur, tebuconazole, tebufloquin, tecloftalam, tecnazene, tecoram, tetraconazole, thiabendazole, thiadifluor, thicyofen, thifluzamide, thiochlorfenphim, thiophanate, thiophanate-methyl, thiram, tiadinil, tioxymid, tolclofos-methyl, tolprocarb, tolylfluanid, triadimefon, triadimenol, triamiphos, triarimol, triazbutil, triazoxide, tributyltin oxide, trichlamide, triclopyricarb, tricyclazole, tridemorph, trifloxystrobin, triflumizole, triforine, triticonazole, validamycin, valifenalate, vinclozolin, zarilamid, zinc naphthenate, flubeneteram, zinc sulfate, zineb, ziram, zoxamide, shiitake mycelium extract, shiitake fruiting body extract, and the like.

Nematicides: aldoxycarb, benclothiaz, cadusafos, DBCP, dichlofenthion, DSP, ethoprophos, fenamiphos, fensulfothion, fluazaindolizine, fluensulfone, fosthiazate, fosthietan, imicyafos, isamidofos, isazofos, oxamyl, thiaxazafen, thionazin, tioxazafen, cyclobutrifluram, and the like.

Pesticides: abamectin, acephate, acequinocyl, acetamiprid, acrinathrin, acynonapyr, afidopyropen, afoxolaner, alanycarb, aldicarb, allethrin, alpha-cypermethrin, alpha-endosulfan, amidoflumet, amitraz, azamethiphos, azinphos-ethyl, azinphos-methyl, azocyclotin, Bacillus thuringiensis, bendiocarb, benfluthrin, benfuracarb, bensultap, benzoximate, benzpyrimoxan, beta-cyfluthrin, beta-cypermethrin, bifenazate, bifenthrin, bioallethrin, bioresmethrin, bistrifluron, broflanilide, bromopropylate, buprofezin, butocarboxim, carbaryl, carbofuran, carbosulfan, cartap, chinomethionat, chlorantraniliprole, chlorethxyfos, chlorfenapyr, chlorfenvinphos, chlorfluazuron, chlormephos, chlorobezilate, chloroprallethrin, chlorpyrifos, chlorpyrifos-methyl, chromafenozide, clofentezine, clothianidin, cyanophos, cyantraniliprole, cyclaniliprole, cycloprothrin, cyenopyrafen, cyflumetofen, cyflumetofen, cyfluthrin, cyhalodiamide, cyhalothrin, cyhexatine, cypermethrin, cyphenothrin, cyromazine, deltamethrin, diacloden, diafenthiuron, diazinon, dichlorvos, dicloromezotiaz, dicofol, dienochlor, diflovidazin, diflubenzuron, dimefluthrin, dimethoate, dimethylvinphos, dinotefuran, diofenolan, disulfoton, DNOC, d-T-80-phthalthrin (d-tetramethrin), emamectin-benzoate, empenthrin, endosulfan, EPN, epsilon-metofluthrin, epsilon-momfluorothrin, esfenvalerate, ethiofencarb, ethiprole, etofenprox, etoxazole, etrimfos, Febantel, fenazaquin, fenbutatin oxide, fenitrothion, fenobucarb, fenothiocarb, fenoxycarb, fenpropathrin, fenpropathrin, fenpyroximate, fenthion, fenvalerate, fipronil, flometoquin, flonicamid, fluacrypyrim, fluazuron, flubendiamide, flucycloxuron, flucythrinate, flufenerim, flufenoxuron, flufenprox, flufiprole, fluhexafon, flumethrin, flupyradifurone, flupyrimin, fluralaner, fluvalinate, fluxametamide, fonophos, formetanate, formothion, furathiocarb, gamma-cyhalothrin, halfenprox, halofenozide, heptafluthrin, hexaflumuron, hexythiazox, hydramethylnon, imidacloprid, imiprothrin, indoxacarb, indoxacarb-MP, isocycloseram, isofenphos, isoprocarb, isoxathion, kappa-bifenthrin, kappa-tefluthrin, lambda-cyhalothrin, lepimectin, lufenuron, malathion, meperfluthrin, metaflumizone, metalcarb, metaldehyde, methacrifos, methamidophos, methidathion, methomyl, methoprene, methoxychlor, methoxyfenozide, methyl bromide, metofluthrin, milbemectin, momfluorothrin, monocrotophos, muscalure, nitenpyram, novaluron, noviflumuron, omethoate, oxazosulfyl, oxydemeton-methyl, oxydeprofos, parathion, parathion-methyl, pentachlorophenol, permethrin, phenothrin, phenthoate, phorate, phosalone, phosmet, phosphamidon, phoxim, pirimicarb, pirimiphos-methyl, Praziquantel, profenofos, profluthrin, propaphos, propargite, prothiofos, protrifenbute, pyflubumide, pymetrozine, pyraclofos, pyrafluprole, pyrethrins, pyridaben, pyridalyl, pyrifluquinazon, pyrimidifen, pyriprole, pyriproxyfen, resmethrin, rotenone, silafluofen, spinetoram, spinosad, spirodiclofen, spiromesifen, spiropidion, spirotetramat, spyromesifen, sulfotep, sulfoxaflor, sulprofos, tau-fluvalinate, tebfenozide, teflubenzuron, tefluthrin, terbufos, tetrachlorantraniliprole, tetrachlorvinphos, tetramethrin, tetramethylfluthrin, tetraniliprole, thiacloprid, thiamethoxam, thiocyclam, thiodicarb, thiofanox, thiometon, tolfenpyrad, tralomethrin, transfluthrin, triazamate, triazuron, trichlorfon, triflumezopyrim, triflumuron, tyclopyrazoflor, vamidothion, zeta-cypermethrin, flupentiofenox, cyetpyrafen, and the like.

In the composition of the present invention, it is also possible to add a surfactant as necessary. Examples of these surfactants include the following (A), (B), (C), (D) and (E).

(A) Nonionic Surfactant:
  (A-1) Polyethylene glycol type surfactant: for example, polyoxyethylene alkyl (for example, $C_{8-18}$) ethers, alkylnaphthol ethylene oxide adducts, polyoxyethylene (mono or di)alkyl (for example, $C_{8-12}$) phenyl ethers, formalin condensates of polyoxyethylene (mono or di)alkyl (for example, $C_{8-12}$) phenyl ethers, polyoxyethylene (mono, di or tri)phenyl phenyl ether, polyoxyethylene (mono, di or tri)benzyl phenyl ether, polyoxypropylene (mono, di or tri)benzyl phenyl ether, polyoxyethylene (mono, di or tri)styrylphenyl ether, polyoxypropylene (mono, di or tri)styrylphenyl ether, polymers of polyoxyethylene (mono, di or tri) styrylphenyl ether, polyoxyethylene polyoxypropylene (mono, di or tri)styrylphenyl ether, polyoxyethylene polyoxypropylene block polymers, alkyl (for example, $C_{8-18}$) polyoxyethylene polyoxypropylene block polymer ethers, alkyl (for example, $C_{8-12}$) phenyl polyoxyethylene polyoxypropylene block polymer ethers, polyoxyethylene bisphenyl ether, polyoxyethylene resin acid ester, polyoxyethylene fatty acid (for example, $C_{8-18}$) monoesters, polyoxyethylene fatty acid (for example, $C_{8-18}$) diesters, polyoxyethylene sorbitan (mono, di or tri)fatty acid (for example, $C_{8-18}$) esters, glycerol fatty acid ester ethylene oxide adducts, castor oil ethylene oxide adducts, hardended castor oil ethylene oxide adducts, alkyl (for example, $C_{8-18}$) amine ethylene oxide adducts and fatty acid (for example, $C_{8-18}$) amide ethylene oxide adducts.
  (A-2) Multivalent alcohol type surfactant: for example, glycerol fatty acid ester, polyglycerin fatty acid ester, pentaerythritol fatty acid ester, sorbitol fatty acid (for example, $C_{8-18}$) esters, sorbitan (mono, di or tri)fatty acid (for example, $C_{8-18}$) esters, sucrose fatty acid esters, multivalent alcohol alkyl ethers, alkyl glycosides, alkyl polyglycosides and fatty acid alkanolamides.
  (A-3) Acetylene type surfactant: for example, acetylene glycol, acetylene alcohol, acetylene glycol ethylene oxide adducts and acetylene alcohol ethylene oxide adducts.
(B) Anionic Surfactant:
  (B-1) Carboxylic acid type surfactant: for example, carboxylic acids such as polyacrylic acid, polymethacrylic acid, polymaleic acid, polymaleic anhydride, maleic acid or copolymers of maleic anhydride and olefin (for example, isobutylene, diisobutylene, etc.), copolymers of acrylic acid and itaconic acid, copolymers of methacrylic acid and itaconic acid, copolymers of maleic acid or maleic anhydride and styrene, copolymers of acrylic acid and methacrylic acid, copolymers of acrylic acid and acrylic acid methyl ester, copolymers of acrylic acid and vinyl acetate, copolymers of acrylic acid and maleic acid or maleic anhydride, polyoxyethylene alkyl (for example, $C_{8-18}$) ether acetic acids, N-methyl-fatty acid (for example, $C_{8-18}$) sarcosinates, resin acids and fatty acids (for example, $C_{8-18}$), and salts of these carboxylic acids.
  (B-2) Sulfate ester type surfactant: for example, sulfate esters such as alkyl (for example, $C_{8-18}$) sulfate esters, polyoxyethylene alkyl (for example, $C_{8-18}$) ether sulfate esters, polyoxyethylene (mono or di)alkyl (for example, $C_{8-12}$) phenyl ether sulfate esters, sulfate esters of polymers of polyoxyethylene (mono or di)alkyl (for example, $C_{8-12}$) phenyl ethers, polyoxyethylene (mono, di or tri)phenyl phenyl ether sulfate ester, polyoxyethylene (mono, di or tri)benzyl phenyl ether sulfate ester, polyoxyethylene (mono, di or tri) styrylphenyl ether sulfate ester, sulfate esters of polymers of polyoxyethylene (mono, di or tri)styrylphenyl ether, sulfate esters of polyoxyethylene polyoxypropylene block polymers, sulfated oils, sulfated fatty acid esters, sulfated fatty acids and sulfated olefins, and salts of these sulfate esters.
  (B-3) Sulfonic acid type surfactant: for example, sulfonic acids such as paraffin (for example, $C_{8-22}$) sulfonic acids, alkyl (for example, $C_{8-12}$) benzene sulfonic acids, formalin condensates of alkyl (for example, $C_{8-12}$) benzene sulfonic acids, formalin condensates of cresol sulfonic acid, α-olefin (for example, $C_{8-16}$)

sulfonic acids, dialkyl (for example, $C_{8-12}$) sulfosuccinic acids, lignin sulfonic acid, polyoxyethylene (mono or di)alkyl (for example, $C_{8-12}$) phenyl ether sulfonic acids, polyoxyethylene alkyl (for example, $C_{8-18}$) ether sulfosuccinic acid half esters, naphthalene sulfonic acid, (mono or di)alkyl (for example, $C_{1-6}$) naphthalene sulfonic acids, formalin condensates of naphthalene sulfonic acid, formalin condensates of (mono or di)alkyl (for example, $C_{1-6}$) naphthalene sulfonic acids, formalin condensates of creosote oil sulfonic acid, alkyl (for example, $C_{8-12}$) diphenyl ether disulfonic acids, igepon T (trade name), copolymers of polystyrene sulfonic acid and styrene sulfonic acid with methacrylic acid, and salts of these sulfonic acids.

(B-4) Phosphate ester type surfactant: for example, phosphate esters such as alkyl (for example, $C_{8-12}$) phosphate esters, polyoxyethylene alkyl (for example, $C_{8-18}$) ether phosphate esters, polyoxyethylene (mono or di)alkyl (for example, $C_{8-12}$) phenyl ether phosphate esters, phosphate esters of polymers of polyoxyethylene (mono, di or tri)alkyl (for example, $C_{8-12}$) phenyl ethers, polyoxyethylene (mono, di or tri)phenyl phenyl ether phosphate ester, polyoxyethylene (mono, di or tri)benzyl phenyl ether phosphate ester, polyoxyethylene (mono, di or tri)styrylphenyl ether phosphate ester, phosphate esters of polymers of polyoxyethylene (mono, di or tri)styrylphenyl ether, phosphate esters of polyoxyethylene polyoxypropylene block polymers, phosphatidylcholine, phosphatidylethanolamine and condensed phosphoric acid (for example, tripolyphosphate, etc.) and salts of these phosphate esters.

As counter ions of salts in the above (B-1) to (B-4), alkali metals (lithium, sodium, potassium, etc.), alkaline earth metals (calcium, magnesium, etc.), ammonium and various amines (for example, alkylamines, cycloalkylamines, alkanolamines, etc.) may be exemplified.

(C) Cationic Surfactant:

For example, alkylamines, alkyl quaternary ammonium salts, alkylamine ethylene oxide adducts and ethylene oxide adducts of alkyl quaternary ammonium salts may be exemplified.

(D) Amphoteric Surfactant:

(D-1) Betaine type surfactant: for example, alkyl (for example, $C_{8-18}$) dimethylaminoacetic acid betaines, acyl (for example, $C_{8-18}$) aminopropyl dimethylaminoacetic acid betaines, alkyl (for example, $C_{8-18}$) hydroxysulfobetaines and 2-alkyl (for example, $C_{8-18}$)—N-carboxymethyl-N-hydroxyethyl imidazolinium betaines may be exemplified.

(D-2) Amino acid type surfactant: for example, alkyl (for example, $C_{8-18}$) amino propionic acids, alkyl (for example, $C_{8-18}$) aminodipropionic acids and N-acyl (for example, $C_{8-18}$)—N'-carboxyethyl-N'-hydroxyethylethylenediamines may be exemplified.

(D-3) Amine oxide type surfactant: for example, alkyl (for example, $C_{8-18}$) dimethyl amine oxides and acyl (for example, $C_{8-18}$) aminopropyl dimethyl amine oxides may be exemplified.

(E) Other Surfactants:

(E-1) Silicon type surfactant: for example, polyoxyethylene/methylpolysiloxane copolymers, polyoxypropylene/methylpolysiloxane copolymers and poly(oxyethylene/oxypropylene)/methylpolysiloxane copolymers may be exemplified.

(E-2) Fluorine type surfactant: for example, perfluoroalkenyl benzene sulfonates, perfluoroalkyl sulfonates, perfluoroalkyl carboxylic acid salts, perfluoroalkenyl polyoxyethylene ethers, perfluoroalkyl polyoxyethylene ethers and perfluoroalkyltrimethylammonium salts may be exemplified.

These surfactants may be used alone or two or more thereof may be used in combination, and the mixing ratio can be freely selected. The content of the surfactant in the composition of the present invention can be appropriately selected, and is preferably in a range of 0.1 parts by weight to 20 parts by weight with respect to 100 parts by weight of the composition of the present invention.

The composition of the present invention may further contain various auxiliary agents. Examples of auxiliary agents that can be used include a thickener, an organic solvent, an antifreezing agent, a defoaming agent, an antibacterial and antifungal agent, and a colorant, and the following agents may be exemplified.

The thickener is not particularly limited, and organic and inorganic natural products, synthetic products and semi-synthetic products can be used, examples of which include heteropolysaccharides such as xanthan gum, welan gum and lamsan gum, water-soluble polymer compounds such as polyvinyl alcohols, polyvinylpyrrolidone, polyacrylic acid, polyacrylic acid sodium and polyacrylamide, cellulose derivatives such as methyl cellulose, carboxymethyl cellulose, carboxyethyl cellulose, hydroxyethyl cellulose and hydroxypropyl cellulose, and smectite clay minerals such as montmorillonite, saponite, hectorite, bentonite, laponite and synthetic smectite. These thickeners may be used alone or two or more thereof may be used in combination, and the mixing ratio can be freely selected. These thickeners may be added without change, or those dispersed in water in advance may be added. In addition, the content in the composition of the present invention can be freely selected.

Examples of organic solvents include alcohols such as ethylene glycol, diethylene glycol, propylene glycol, dipropylene glycol and isopropanol, ethers such as butyl cellosolve, ketones such as cyclohexanone, esters such as γ-butyrolactone, acid amides such as N-methylpyrrolidone and N-octylpyrrolidone, aromatic hydrocarbons such as xylene, alkylbenzenes, phenylxysilylethane and alkylnaphthalenes, aliphatic hydrocarbons such as machine oil, normal paraffin, isoparaffin and naphthene, mixtures of aromatic hydrocarbons such as kerosene and aliphatic hydrocarbons, and oils and fats such as soybean oil, linseed oil, rapeseed oil, coconut oil, cottonseed oil and castor oil.

As the antifreezing agent, for example, ethylene glycol, diethylene glycol, propylene glycol, and glycerin can be used. Propylene glycol and glycerin are preferable. In addition, the content in the composition of the present invention can be freely selected.

A defoaming agent such as a silicone type emulsion, an antibacterial and antifungal agent, a colorant, and the like may be additionally added.

A method for producing the composition of the present invention is not particularly limited, and the composition is obtained by adding the above components to a dispersion medium and mixing them with a stirrer. In addition, as necessary, an agrochemical active component, a surfactant and other auxiliary agents alone or in combination may be finely pulverized by a dry or wet pulverizer.

Dry pulverization can be performed with a hammer mill, a pin mill, a jet mill, a ball mill, a roll mill or the like. Fine pulverization by wet pulverization can be performed by a wet pulverizer such as an inline mill or a bead mill.

The composition of the present invention can be used as an herbicide for a paddy field in any treatment method of soil treatment and foliage treatment under flooding. Preferably, it can be used in a treatment method with foliage treatment. Examples of lowland weeds include Gramineae weeds represented by Chinese sprangletop (*Leptochloa chinensis*), bearded sprangletop (*Leptochloa fascicularis*), barnyard grass (*Echinochloa crus-galli*), junglerice (*Echinochloa colonum*), late watergrass (*Echinochloa oryzicola*), southern cutgrass (*Leersia hexandra*), knotgrass (*Paspalum distichum*), saramollagrass (*Ischaemum rugosum*), itchgrass (*Rottboellia cochinchinensis*), broadleaf signalgrass (*Brachiaria platyphylla*), Alexandergrass (*Brachiaria growthaginea*), large crabgrass (*Digitaria sanguinalis*), crowfoot grass (*Dactyloctenium aegyptium*), goosegrass (*Eleusine indica*), red rice (*Oryza sativa*), bermuda grass (*Cynodon dactylon*), and fall panicum (*Panicum dichotomiflorum*), Cyperaceae weeds represented by *Eleocharis kuroguwai*, globe fringerush (*Fimbristylis miliacea*), Japanese bulrush (*Schoenoplectus juncoides*), *Schoenoplectus nipponicus*, ricefield bulrush (*Schoenoplectus mucronatus*), *Cyperus serotinus*, smallflower umbrella sedge (*Cyperus difformis*), rice flat sedge (*Cyperus iria*), purple nutsedge (*Cyperus rotundus*), yellow nutsedge (*Cyperus esculentus*), and cosmopolitan bulrush (*Bolboschoenus martimus*), Alismataceae weeds represented by water plantain (*Alisma canaliculatum*), pygmy arrowhead (*Sagittaria pygmaea*), and threeleaf arrowhead (*Sagittaria trifolia*), Commelinaceae weeds represented by Asian spiderwort (*Murdannia keisak*) and Bengal dayflower (*Commelina benghalensis*), Pontederiaceae weeds represented by heartleaf false pickerelweed (*Monochoria korsakowii*), oval-leafed pondweed (*Monochoria vaginalis*), ducksalad (*Heteranthera limosa*), and water hyacinth (*Eichhornia crassipes*), Elatinaceae weeds represented by threestamen waterwort (*Elatine triandra*), Lythraceae weeds represented by redstem (*Ammannia coccinea*) and Indian toothcup (*Rotala indica*), Oenotheraceae weeds represented by *Ludwigia epilobioides* and Mexican primrose-willow (*Ludwigia octovalvis*), Scrophulariaceae weeds represented by rushlike dopatrium (*Dopatrium junceum*), *Gratiola japonica*, dwarf ambulia (*Limnophila sessiliflora*), prostrate false pimpernel (*Lindernia pyxidaria*), and yellowseed false pimpernel (*Lindernia dubia*), Amaranthaceae weeds represented by alligator weed (*Alternanthera philoxeroides*) and spiny amaranth (*Amaranthus spinosus*), Polygonaceae weeds represented by water pepper (*Polygonum hydropiper*), Sphenocleaceae weeds represented by gooseweed (*Sphenoclea zeylanica*), Fabaceae weeds represented by Indian jointvetch (*Aeschynomene indica*) and hemp *sesbania* (*Sesbania exaltata*), Asteraceae weeds represented by devil's beggarticks (*Bidens frondosa*), threelobe beggarticks (*Bidens tripartita*), false daisy (*Echpta prostrata*), and goatweed (*Ageratum conyzoides*), Convolvulaceae weeds represented by swamp morningglory (*Ipomoea aquatica*), Marsileaceae weeds represented by water clover (*Marsilea minuta*), Lemnaceae weeds represented by common duckmeat (*Spirodela polyrhiza*) and duckweed (*Lemna paucicostata*), and Potamogetonaceae weeds represented by roundleaf pondweed (*Potamogeton distinctus*).

In addition, the composition of the present invention can be used as an herbicide for farmlands and orchards in any treatment method of soil treatment, soil incorporation treatment and foliage treatment. Examples of farmland weeds include Poaceae weeds represented by fall panicum (*Panicum dichotomiflorum*), shattercane (*Sorghum bicolor*), johnson grass (*Sorghum halepense*), barnyard grass (*Echinochloa crus-galli* var. *crus-galli*), cockspur grass (*Echinochloa crus-galli* var. *praticola*), Japanese barnyard millet (*Echinochloa utilis*), southern crabgrass (*Digitaria ciliaris*), sourgrass (*Digitaria insularis*), jamaican crabgrass (*Digitaria horizontalis*), wild oat (*Avena fatua*), blackgrass (*Alopecurus myosuroides*), shortawn foxtail (*Alopecurus aequalis*), windgrass (*Apera spica-venti*), downy brome (*Bromus tectorum*), Italian ryegrass (*Lolium multiflorum*), rigid ryegrass (*Lohum rigidum*), littleseed canarygrass (*Phalaris minor*), annual bluegrass (*Poa annua*), goosegrass (*Eleusine indica*), green foxtail (*Setaria viridis*), giant foxtail (*Setaria faberi*), signalgrass (*Brachiaria decumbens*), and southern sandbur (*Cenchrus echinatus*), Cyperaceae weeds represented by purple nutsedge (*Cyperus rotundus*), Solanaceae weeds represented by black nightshade (*Solanum nigrum*) and jimsonweed (*Datura stramonium*), Malvaceae weeds represented by velvetleaf (*Abutilon theophrasti*) and prickly sida (*Sida spinosa*), Convolvulaceae weeds represented by tall morning-glory (*Ipomoea purpurea*), ivyleaf morning-glory (*Ipomoea hederacea*), and Japanese bindweed (*Calystegia hederacea*), Amaranthaceae weeds represented by purple amaranth (*Amaranthus lividus*), redroot pigweed (*Amaranthus retroflexus*), palmer amaranth (*Amaranthus palmeri*), and tall waterhemp (*Amaranthus tuberculatus*), Asteraceae weeds represented by common cocklebur (*Xanthium strumarium*), common ragweed (*Ambrosia artemisiifolia*), giant ragweed (*Ambrosia trifida*), horseweed (*Conyza canadensis*), common sunflower (*Helianthus annuus*), pineappleweed (*Matricaria matricarioides*), hairy galinsoga (*Galinsoga ciliata*), Canada thistle (*Cirsium arvense*), common groundsel (*Senecio vulgaris*), and annual fleabane (*Erigeron annuus*), Brassicaceae weeds represented by variableleaf yellowcress (*Rorippa* indica), wild mustard (*Sinapis arvensis*), and shepherd's purse (*Capsella bursa pastoris*), Polygonaceae weeds represented by oriental lady's thumb (*Persicaria longiseta*) and wild buckwheat (*Polygonum convolvulus*), Portulacaceae weeds represented by common purslane (*Portulaca oleracea*), Chenopodiaceae weeds represented by lambsquarters (*Chenopodium album*), figleaved goosefoot (*Chenopodium ficifolium*), kochia (*Kochia scoparia*), and Russian thistle (*Salsola tragus*), Caryophyllaceae weeds represented by common chickweed (*Stellaria media*), Plantaginaceae weeds represented by Persian speedwell (*Veronica persica*), Commelinaceae weeds represented by Asiatic dayflower (*Commelina communis*) and Benghal dayflower (*Commelina benghalensis*), Lamiaceae weeds represented by henbit (*Lamium amplexicaule*) and purple deadnettle (*Lamium purpureum*), Euphorbiaceae weeds represented by wild poinsettia (*Euphorbia heterophylla*) and spotted spurge (*Euphorbia maculata*), Rubiaceae weeds represented by false cleavers (*Galium spurium*) and Asian madder (*Rubia* akane), Violaceae weeds represented by pansy (*Viola tricolor*), Papaveraceae weeds represented by field poppy (*Papaver rhoeas*), Fabaceae weeds represented by hemp *sesbania* (*Sesbania exaltata*) and sicklepod (*Cassia obtusifolia*), and Oxalidaceae weeds represented by creeping woodsorrel (*Oxalis corniculata*).

In addition, the composition of the present invention can remove a wide range of weeds that occur in, for example, embankment slopes, riverbeds, road shoulders and slopes, railroad floors, park green spaces, grounds, parking lots, airports, industrial facility lands such as factories and storage facilities, fallow lands, non-agricultural lands in which it is necessary to control weed growth such as unused lands in cities, or orchards, meadows, lawn grassess, forestry lands and the like. The weeds include, in addition to those described as weeds for farmlands and orchards, annual bluegrass (*Poa annua*), dandelion (*Taraxacum officinale*), hairy fleabane (*Conyza bonariensis*), horseweed (*Conyza canadensis*), Guernsey fleabane (*Conyza sumatrensis*), wavy bittercress (*Cardamine flexuosa*), white clover (*Trifolium repens*), lawn pennywort (*Hydrocotyle sibthorpioides*), Chinese plantain (*Plantago asiatica*), green kyllinga (*Kyllinga brevifolia*), field horsetail (*Equisetum arvense*), and the like.

The composition of the present invention acts on useful plants or is used in a place in which useful plants are to be grown or are growing or in non-agricultural lands at the same time or in a divided manner, and can control growth of undesirable plants for the sake of useful plants. Here, the useful plants include field crops, lowland crops, garden crops, lawn grasses, fruit trees and the like.

Here, specifically, the useful plants referred to in the present invention include, for example, crops such as corn, rice, wheat, barley, rye, oat, sorghum, cotton, soybean, peanut, buckwheat, sugar beet, rapeseed, sunflower, sugar cane and tobacco; vegetables such as Solanaceae vegetables (eggplant, tomato, pepper, red pepper, potato, etc.), Cucurbitaceae vegetables (cucumber, pumpkin, zucchini, watermelon, melon, etc.), Brassicaceae vegetables (radish, turnip, horseradish, kohlrabi, Chinese cabbage, cabbage, mustard, broccoli, cauliflower, etc.), Asteraceae vegetables (burdock, crowndaisy, artichoke, lettuce, etc.), Liliaceae vegetables (green onion, onion, garlic, asparagus), Umbelliferae vegetables (carrot, parsley, celery, parsnip, etc.), Chenopodiaceae vegetables (spinach, leaf beet, etc.), Labiatae vegetables (beefsteak plant, mint, basil, etc.), strawberry, sweet potato, yam and taro; fruits such as pomaceous fruits (apple, European pear, Japanese pear, Chinese quince, quince, etc.), stone fruits (peach, plum, nectarine, Japanese apricot, sweet cherry, apricot, prune, etc.), citrus fruits (Satsuma mandarins, orange, lemon, lime, grapefruit, etc.), nuts (chestnuts, walnuts, hazelnuts, almonds, pistachios, cashew nuts, macadamia nuts, etc.), berry fruits (blueberries, cranberries, blackberries, raspberries, etc.), grape, persimmon, olive, loquat, banana, coffee, date palm, coconut and oil palm; trees other than fruit trees such as tea, mulberry, street trees (*Fraxinus japonica*, birch tree, dogwood, eucalyptus, ginkgo, lilac, maple, oak, poplar, cercis, maple, plane tree, zelkova, Japanese arborvitae, Japanese fir, hemlock spruce, *Juniperus rigida*, pine tree, spruce tree, yews, *Ulmus campestris, Aesculus turbinata*, etc.), sweet *viburnum, Podocarpus macrophyllus, Cryptomeria japonica*, Japansese cypress, croton, *Euonymus japonica* and Japanese *photinia*; lawn grasses such as *Zoysia* (*Zoysia japonica, Zoysia matrella*, etc.), Bermudagrass (Bermuda Grass, etc.), bent grass (*Agrostis gigantea, Agrostis stolonifera, Agrostis capillaris*, etc.), bluegrass (Kentucky bluegrass, *Poa annua*, etc.), fescue (fescue grass, *Festuca rubra* var. *commutata, Festuca rubra* var., etc.), ryegrass (*Lolium multiflorum* Lam., *Lolium perenne*, etc.), *Dactylis glomerata* and *Phleum pratense*; oil crops such as palm oil and Jatropha curcas; flowers and ornamental plants (*Rosa polyantha, Dianthus caryophylus*, chrysanthemum, *Eustoma russellianum*, baby's breath, *gerbera*, marigold, *Salvia splendens, petunia, verbena*, tulip, aster, *Gentiana scabra*, lily, pansy, Cyclamen persicum, orchid, *Convallaria* herb, *Lavandula* vera, stock, ornamental cabbage, *primula*, poinsettia, *gladiolus*, cattleya, daisy, *verbena*, cymbidium, *begonia*, etc.); foliage plants and the like, but the present invention is not limited thereto.

The composition of the present invention can be applied by, for example, a method in which it is diluted with a stock solution or water by a factor of about 50 to 5,000, and sprayed on crops or trees or the soil in which they grow using a sprayer or the like, or a method in which it is diluted with a stock solution or water by a factor of about 2 to 100 and sprayed from the air using a helicopter or the like.

Compared with the composition including the amorphous Compound (1), for example, the composition of the present invention has an excellent storage stability, fluidity, and herbicidal effect so that Compound (1) in the composition does not solidify.

In particular, these are significant when the composition of the present invention is a suspension-type formulation or an aqueous suspension-type formulation.

EXAMPLES

Hereinafter, the present invention will be described in more detail using production examples of the crystal of the present invention as examples, but the present invention is not limited thereto.

Here, various measurement conditions are as follows.
[Powder X-Ray Diffraction Measurement Conditions]
  Device: X'PERT-PRO MPD (commercially available from Spectris)
  Measurement method: transmission method
  X rays: Cu-Kα
  Voltage: 45 kV
  Current: 40 mA
  Sampling interval: 0.0070 deg
  Data range: 2θ=5 deg to 40 deg
[Differential Scanning Calorimetry Conditions]
  Device: DSC-60 (commercially available from Shimadzu Corporation)
  Temperature rise: 20° C.-(10° C./min)–450° C.
  Atmosphere: nitrogen
  Control: $Al_2O_3$
  Container: made of SUS
  Sampling: 1 sec

[Production Example 1]: Production of Crystal of Present Invention, Part 1

14.90 g of thionyl chloride was added to a solution in which 34.83 g of 3-[(isopropylsulfonyl)methyl]-5-(trifluoromethyl)-[1,2,4]triazolo[4,3-a]pyridine-8-carboxylic acid and 348.30 g of 1,2-dichloroethane were mixed under reflux heating. After the addition was completed, the reaction mixture was stirred for 4.5 hours under reflux heating. After the stirring was completed, 80.62 g of a solvent was distilled off at 60° C. under a reduced pressure. After the distillation was completed, 9.83 g of 5-methyl-1,3,4-oxadiazole-2-amine and 174.20 g of 1,2-dichloroethane were added at 60° C. After the addition was completed, 179.00 g of the solvent of the reaction mixture was distilled off at 60° C. under a reduced pressure. After the distillation was completed, 175.00 g of 1,2-dichloroethane, 2.51 g of potassium acetate, and 175.00 g of water were added at 60° C. and liquid separation was performed. The obtained aqueous layer was extracted with 175.00 g of 1,2-dichloroethane. After the obtained organic layer was washed with water, 307.45 g of the solvent was distilled off at 70° C. under a reduced pressure. After the distillation was completed, 209.00 g of 1,4-dioxane was added at 70° C. to the obtained slurry. After the addition was completed, the obtained slurry was cooled to −2° C. at a cooling rate of 25° C. per hour, stirred at the same temperature for 1 hour, and then filtered. The obtained crystal was washed with 105.00 g of ethyl acetate at 0° C., and then dried under a reduced pressure, and thereby 31.40 g of a target crystal was obtained.

The powder X-ray diffraction of the obtained crystal was measured, and as a result, the diffraction pattern shown in FIG. 1 was obtained.

Figure 2:
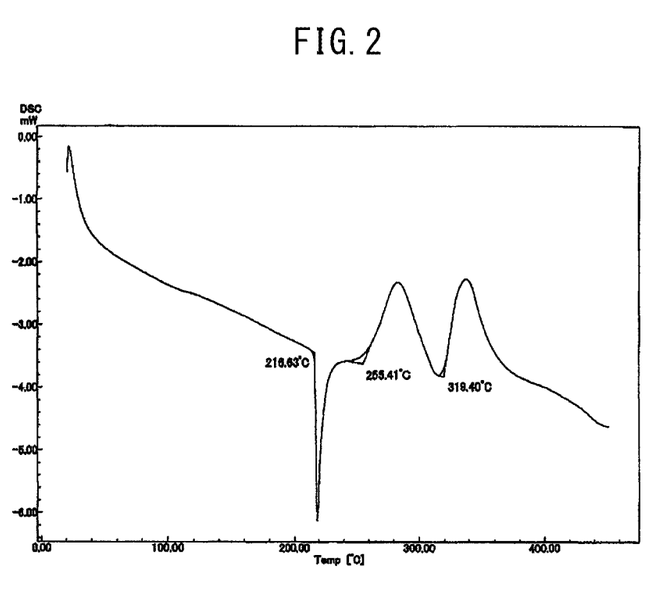
FIG. 2 is differential scanning calorimetry chart of the crystal of the present invention.

In addition, differential scanning calorimetry of the obtained crystal was performed, and as a result, the peak pattern shown in FIG. 2 was obtained.

[Production Example 2]: Production of Crystal of Present Invention, Part 2

4.10 g of thionyl chloride was added to a solution in which 9.93 g of 3-[(isopropylsulfonyl)methyl]-5-(trifluoromethyl)-[1,2,4]triazolo[4,3-a]pyridine-8-carboxylic acid and 99.3 g of 1,2-dichloroethane were mixed under reflux heating. After the addition was completed, the reaction mixture was stirred for 4 hours under reflux heating. After the stirring was completed, 20.5 g of a solvent was distilled off at 60° C. under a reduced pressure. After the distillation was completed, 2.80 g of 5-methyl-1,3,4-oxadiazole-2-amine and 49.7 g of 1,2-dichloroethane were added at 60° C. After the addition was completed, 66.5 g of the solvent of the reaction mixture was distilled off at 60° C. under a reduced pressure. After the distillation was completed, 66.5 g of 1,2-dichloroethane was added at 60° C. After the addition was completed, 56.6 g of the solvent of the reaction mixture was distilled off at 60° C. under a reduced pressure. After the distillation was completed, 56.6 g of 1,2-dichloroethane, 0.69 g of potassium acetate and 44.7 g of water were added at 60° C., and liquid separation was performed. The obtained aqueous layer was extracted with 39.7 g of 1,2-dichloroethane. After the obtained organic layer was washed with water, 69.5 g of the solvent was distilled off at 60° C. under a reduced pressure. After the distillation was completed, 9.93 g of N,N-dimethylformamide was added to the obtained slurry at 60° C. After the addition was completed, the mixed solution was stirred at 85° C. to dissolve a crystal. While the mixed solution was cooled to 60° C. and stirred, 5 mg of a target seed crystal (using the target crystal obtained in Production Example 1) was added. After the addition was completed, stirring was continued at 60° C., crystal precipitation was visually confirmed, and the mixture was then cooled to −2° C. at a cooling rate of 30° C. per hour. The obtained slurry was stirred at −2° C. for 3 hours and then filtered. The obtained crystal was washed with 9.93 g of 1,2-dichloroethane at 0° C. and then dried under a reduced pressure, and thereby 9.51 g of a target crystal was obtained.

The powder X-ray diffraction of the obtained crystal was measured, and as a result, the diffraction pattern shown in FIG. 1 was obtained.

In addition, differential scanning calorimetry of the obtained crystal was performed, and as a result, the peak pattern shown in FIG. 2 was obtained.

[Production Example 3]: Production of Crystal of Present Invention, Part

Process 1: Synthesis of 3-[(isopropylsulfonyl)methyl]-5-(trifluoromethyl)-[1,2,4]triazolo[4,3-a]pyridine-8-carbonyl Chloride 0.43 g of thionyl chloride was added under reflux heating to a solution in which 1.00 g of 3-[(isopropylsulfonyl)methyl]-5-(trifluoromethyl)-[1,2,4]triazolo[4,3-a]pyridine-8-carboxylic acid and 10 g of toluene were mixed. After the addition was completed, the reaction mixture was stirred for 1 hour under reflux heating. After the stirring was completed, the solvent was distilled off under a reduced pressure, and thereby 1.10 g of a target light brown solid was obtained.

Melting point: 140° C. to 142° C.

Process 2: Production of Crystal of Present Invention 0.285 g of 5-methyl-1,3,4-oxadiazole-2-amine was added to a solution in which 1.10 g of 3-[(isopropylsulfonyl)methyl]-5-(trifluoromethyl)-[1,2,4]triazolo[4,3-a]pyridine-8-carbonyl chloride and 10 g of toluene were mixed at room temperature. After the addition was completed, the reaction mixture was stirred for 2 hours under reflux heating. After the stirring was completed, the reaction mixture was cooled to room temperature. The obtained slurry was stirred at room temperature for 1 hour and then filtered. The obtained crystal was washed with 5.0 g of toluene at room temperature and then dried under a reduced pressure, and thereby 1.00 g of a target crystal was obtained. The powder X-ray diffraction of the obtained crystal was measured, and as a result, the diffraction pattern shown in FIG. 1 was obtained.

[Production Example 4]: Production of Crystal of Present Invention, Part 4

Process 1: Synthesis of 3-[(isopropylsulfonyl)methyl]-5-(trifluoromethyl)-[1,2,4]triazolo[4,3-a]pyridine-8-carbonyl Chloride 0.43 g of thionyl chloride was added under reflux heating to a solution in which 1.00 g of 3-[(isopropylsulfonyl)methyl]-5-(trifluoromethyl)-[1,2,4]triazolo[4,3-a]pyridine-8-carboxylic acid and 10 g of 1,2-dichloroethane were mixed. After the addition was completed, the reaction mixture was stirred for 4 hours under reflux heating. After the stirring was completed, the solvent was distilled off under a reduced pressure, and thereby 1.08 g of a target light brown solid was obtained.

Process 2: Production of Crystal of Present Invention 0.285 g of 5-methyl-1,3,4-oxadiazole-2-amine was added to a solution in which 1.08 g of 3-[(isopropylsulfonyl)methyl]-5-(trifluoromethyl)-[1,2,4]triazolo[4,3-a]pyridine-8-carbonyl chloride and 10 g of 1,2-dichloroethane were mixed at room temperature. After the addition was completed, the reaction mixture was stirred for 3 hours under reflux heating. After the stirring was completed, the reaction mixture was cooled to room temperature. The obtained slurry was stirred at room temperature for 1 hour and then filtered. The obtained crystal was washed with 3.0 g of 1,2-dichloroethane at room temperature, and then dried under a reduced pressure, and thereby 0.484 g of a target crystal was obtained.

The powder X-ray diffraction of the obtained crystal was measured, and as a result, the diffraction pattern shown in FIG. 1 was obtained.

[Reference Example 1]: Production of Amorphous Compound (1)

Production was performed according to the description of Synthesis Example 2 in examples in WO 2014/192936.

131.1 mg of 1-ethyl-3-(3-dimethylaminopropyl)carbodiimide hydrochloride and 93.2 mg of 1-hydroxy-7-azabenzotriazole were added at room temperature to a solution in which 200 mg of 3-[(isopropylsulfonyl)methyl]-5-(trifluoromethyl)-[1,2,4]triazolo[4,3-a]pyridine-8-carboxylic acid, 67.8 mg of 5-methyl-1,3,4-oxadiazole-2-amine and 5 ml of N,N-dimethylformamide were mixed. After the addition was completed, the reaction mixture was stirred at room temperature for 24 hours. After the stirring was completed, water was added to stop the reaction, and extraction with chloroform (10 ml×1 time) was then performed. The obtained organic layer was washed with water and then dried with anhydrous sodium sulfate, and the solvent was distilled off under a reduced pressure. The obtained residue was purified through silica gel chromatography {n-hexane:ethyl acetate:methanol=50:50:0 to 0:100:0 to 0:80:20 (volume ratio)} to obtain 204.4 mg of the amorphous Compound (1).

Figure 3:
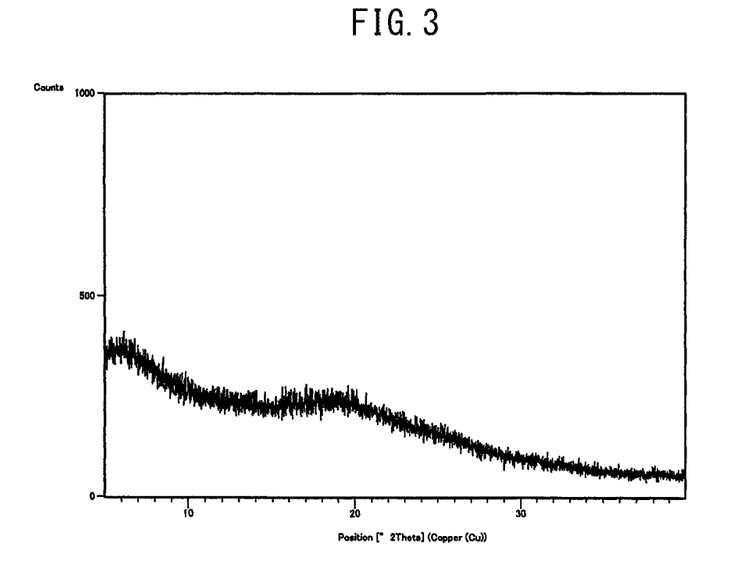
FIG. 3 is a powder X-ray diffraction chart of amorphous Compound (1) in Reference Example 1.

The powder X-ray diffraction of the obtained amorphous compound was measured, and as a result, the diffraction pattern shown in FIG. 3 was obtained.

Figure 4:
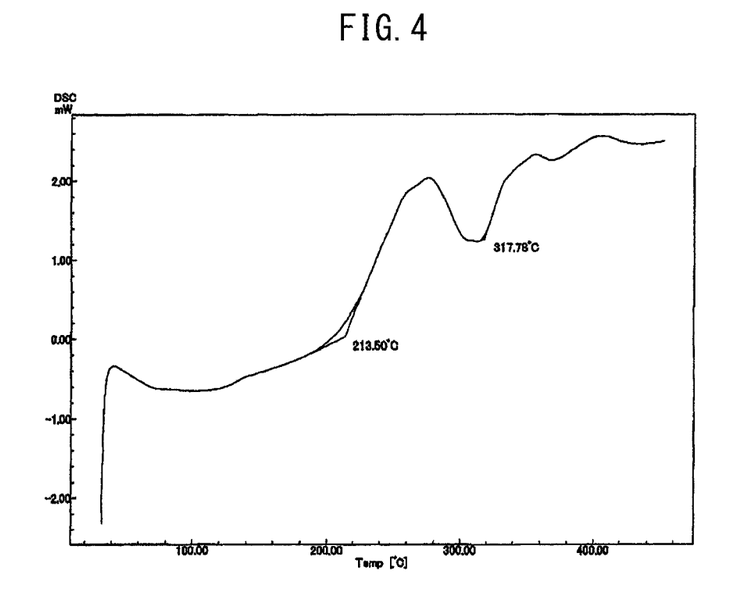
FIG. 4 is a differential scanning calorimetry chart of amorphous Compound (1) in Reference Example 1.

In addition, differential scanning calorimetry of the obtained amorphous compound was performed, and as a result, the peak pattern shown in FIG. 4 was obtained.

INDUSTRIAL APPLICABILITY

According to the present invention, it is possible to produce a crystal of Compound (1).

The invention claimed is:

1. A crystal of a heterocyclic amide compound represented by Formula (1), which has peaks at a diffraction angle 2θ of 7.29°±0.2, 12.62°±0.2, 14.13°±0.2, 17.51°±0.2, 18.64°±0.2, 19.03°±0.2, 20.56°±0.2, 20.89°±0.2, 21.76°±0.2, 23.37°±0.2, 25.41°±0.2, 27.70°±0.2 and 30.34°±0.2 in powder X-ray diffraction with Cu-Kα rays:

(1)

2. A suspension composition including the crystal according to claim 1 and a dispersion medium.

3. A weed control method, comprising a process of applying the suspension composition according to claim 2 in an amount effective for controlling weeds.

* * * * *